United States Patent
Tamura et al.

(10) Patent No.: US 7,964,683 B2
(45) Date of Patent: Jun. 21, 2011

(54) BIOCOMPATIBLE POLYMERIC COMPOUND, BIOCOMPATIBLE POLYMER AND POLYMER PARTICLES

(75) Inventors: Takashi Tamura, Kanagawa (JP); Kazuya Takeuchi, Kanagawa (JP); Masahiko Taniguchi, Kanagawa (JP); Kazuhiro Aikawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/502,708

(22) Filed: Jul. 14, 2009

(65) Prior Publication Data

US 2010/0016534 A1 Jan. 21, 2010

(30) Foreign Application Priority Data

Jul. 15, 2008 (JP) .................................. 2008-183441

(51) Int. Cl.
*C08F 30/02* (2006.01)
(52) U.S. Cl. ...................................................... 526/277
(58) Field of Classification Search .................... 526/277
See application file for complete search history.

(56) References Cited

U.S. PATENT DOCUMENTS

| 5,019,370 | A | 5/1991 | Jay et al. |
| 5,686,061 | A | 11/1997 | Li et al. |
| 2007/0098640 | A1 | 5/2007 | Bonitatebus, Jr. et al. |
| 2007/0098641 | A1 | 5/2007 | Bonitatebus, Jr. et al. |
| 2007/0098642 | A1 | 5/2007 | Bonitatebus, Jr. et al. |

FOREIGN PATENT DOCUMENTS

| JP | 2870727 | 1/1999 |
| WO | 2006/106513 | 10/2006 |

OTHER PUBLICATIONS

STN HCAPLUS structure search result RN 104257-20-7, JP 60204791, Nakaya et al., 1985.*

Zheng-Rong Lu et al—Polymer platforms for drug delivery and biomedical imaging—Journal of Controlled Release—Received Apr. 26, 2007; accepted Jun. 19, 2007. Available online Jun. 27, 2007—pp. 269-277.
Fabien Hyafil et al.—Noninvasive detection of macrophages using a nanoparticulate contrast agent for computed tomography—Nature medicine—vol. 13, No. 5, May 2007, pp. 636-641.
Cathrine Christiansen—X-ray contrast media—an overview—Toxicology 209 (2005), pp. 185-187.
Kobunshi Ronbunshu—The Society of Polymer Science, Japan—vol. 35, No. 7, pp. 423-427 , Jul. 1978.
Charles H Reynolds et al—Gadolinium-Loaded Nanoparticle: New Contrast Agents for Magnetic Resonance Imaging—J. Am. Chem. Soc. 2000, 122, 8940-8945 , Received Apr. 24, 2000.

* cited by examiner

*Primary Examiner* — Ling-Siu Choi
*Assistant Examiner* — Sonya Wright
(74) *Attorney, Agent, or Firm* — Young & Thompson

(57) ABSTRACT

The compound represented by general formula (I) below:

General formula (I)

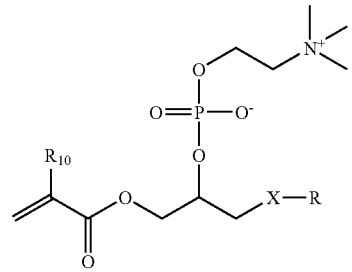

wherein $R^{10}$ represents hydrogen atom or methyl group; X represents —O(C=O)— or the like; and R represents hydrogen atom, a substituted or unsubstituted alkyl group, a substituted or unsubstituted aryl group, or the like, and a polymer obtained by polymerizing a polymeric compound comprising the compound, which are useful for manufacturing hydrophilic polymer materials of high biocompatibility.

4 Claims, No Drawings

US 7,964,683 B2

BIOCOMPATIBLE POLYMERIC COMPOUND, BIOCOMPATIBLE POLYMER AND POLYMER PARTICLES

CROSS-REFERENCE TO RELATED APPLICATIONS

This application claims benefit of priority under 35 USC 119 to Japanese Patent Application No. 2008-183441 filed on Jul. 15, 2008, the disclosure of which is expressly incorporated by reference herein in its entirety.

TECHNICAL FIELD

The present invention relates to polymeric compounds. More particularly, the present invention relates to a new polymeric compound, having surfactant properties combining both hydrophilic and hydrophobic groups, that is useful for manufacturing hydrophilic polymer materials of high biocompatibility. The present invention further relates to polymers obtained by polymerizing the aforementioned compounds, and to particles of minute particle diameter containing the polymers.

BACKGROUND ART

In recent years, materials comprised chiefly of hydrophilic polymers have been widely employed in artificial organs, artificial muscle, medicinal drug carriers, cellular scaffolding materials, agricultural materials (moisture-retaining agents), and the like.

Examples of natural hydrophilic polymers include alginates, collagen, hyaluronic acid, chondroitin sulfate, fibrin, chitosan, and silk. These polymers are of high biocompatibility, but present problems in the form of high biodegradability and low mechanical strength. Contamination by pathogens is also a concern.

Examples of artificially synthesized hydrophilic polymers include polyethylene glycol, polysodium acrylate, polyacrylamide, polylactic acid, polyhydroxyethyl methacrylate, and polyacrylamidomethylpropane sulfuric acid. These polymers are of high mechanical strength and present little risk of contamination by pathogens. However, they present a problem in the form of low biocompatibility. There is also a problem in that some of these polymers are highly toxic.

In recent years, a polymer material that is highly biocompatible and hydrophilic has been provided by employing 2-methacryloyloxyethyl phosphorylcholine (MPC) (Collected Papers on Polymers, 1978, Vol. 35, No. 7, pp. 423-427; and Japanese Patent No. 2870727, the disclosures of which are expressly incorporated by reference herein in their entireties). The phosphatidyl choline moiety in polymers manufactured with MPC has a structure similar to that of phospholipids, which are compounds found within the body. The fact that this moiety is charge neutral and highly hydrophilic is a factor that increases its biocompatibility.

However, the high solubility in water of 2-methacryloyloxyethyl phosphorylcholine complicates synthesis. Polymers comprising a high ratio of 2-methacryloyloxyethyl phosphorylcholine present problems in that they are too hydrophilic to form particles in water, and have low mechanical strength.

Recently, drug delivery technology has been employed to selectively accumulate imaging agents in affected areas in an attempt to heighten the contrast of images of affected areas and reduce the quantity of imaging agent administered.

For example, the encasing of a drug or the like in the form of an imaging agent within a particle such as a liposome or micelle and the modification of the surface of the particle with a ligand molecule or the like, and the coating of drugs with polymers, have been reported (U.S. Pat. Nos. 5,686,061 and 5,019,370; International Patent Application Publication No. 06106513; U.S. Patent Application Publication Nos. 2007098640, 2007098641, and 2007098642; J. Am. Chem. Soc. 2000, 122, 8940-8945; J. Control. Release 2007, 122, 269-277; and Nature Medicine 2007, 13, 636-641, the disclosures of which are expressly incorporated by reference herein in their entireties). However, such imaging agents have low stability and low safety, and large particle size, and tend to be captured by the reticuloendothelial system, and the like, thereby compromising imaging performance.

Iodine-containing compounds, for example, are known X-ray imaging agents. Triiode benzenes are employed in vascular imaging and urethrography. However, most X-ray imaging agents are water-soluble compounds of low molecular weight, and do not remain in the blood long following administration. Thus, imaging must be conducted immediately after administering the imaging agent. Toxicity when a large quantity of imaging agent is employed is frequently reported (Toxicology 2005, 209, 185-187, the disclosure of which is expressly incorporated by reference herein in its entirety).

DISCLOSURE OF THE INVENTION

The object of the present invention is to provide a new polymeric compound that is useful for manufacturing hydrophilic polymer materials of high biocompatibility. A further object of the present invention is to provide a polymer that is manufactured by polymerizing such a polymeric compound.

The present inventors conducted extensive research into achieving the above objects, resulting in the discovery of a new polymeric compound suited to the manufacturing of polymers similar to highly biocompatible phospholipids. The present invention was achieved on the basis of these findings.

The present invention thus provides [1] to [12] below:

[1] A compound represented by general formula (I) below:

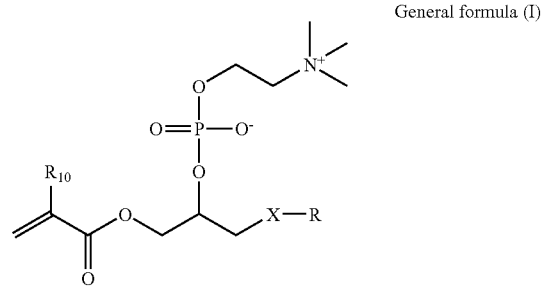

General formula (I)

wherein $R^{10}$ represents hydrogen atom or methyl group; X represents —O—, —S—, —NR$^2$—, or —O(C=O)—; $R^2$ represents hydrogen atom, a substituted or unsubstituted alkyl group, or a substituted or unsubstituted aryl group; and R represents hydrogen atom, a substituted or unsubstituted alkyl group, a substituted or unsubstituted alkenyl group, a substituted or unsubstituted cycloalkyl group, a substituted or unsubstituted cycloalkenyl group, a substituted or unsubstituted heterocyclic group, or a substituted or unsubstituted aryl group.

[2] The compound according to [1], wherein X is —O(C=O)—.
[3] The compound according to [1] or [2], wherein R is a substituted or unsubstituted alkyl group.
[4] The compound according to [3], wherein R is a C1 to C20 unsubstituted alkyl group.
[5] The compound according to [1] or [2], wherein R is a substituted or unsubstituted aryl group.
[6] The compound according to [5], wherein R comprises two or more iodine atoms.
[7] The compound according to [5], wherein R is an iodine-substituted phenyl group comprising two or more iodine atoms, with the iodine-substituted phenyl group being optionally substituted with a substituent selected from the group consisting of amino group, carboxyl group, a halogen atom, —NR$^3$(C=O)R$^4$, —(C=O)OR$^5$, —(C=O)NR$^6$R$^7$ (with each of R$^3$ to R$^7$ representing hydrogen atom, a substituted or unsubstituted alkyl group, or a substituted or unsubstituted aryl group), a substituted or unsubstituted alkyl group, and a substituted or unsubstituted aryl group.
[8] The compound according to [7], wherein R is an iodine-substituted phenyl group substituted with three iodine atoms.
[9] A polymer obtained by polymerization reaction of a composition comprising the compound according to any one of [1] to [8].
[10] A polymer comprising the structural unit represented by general formula (11) below:

General formula (11)

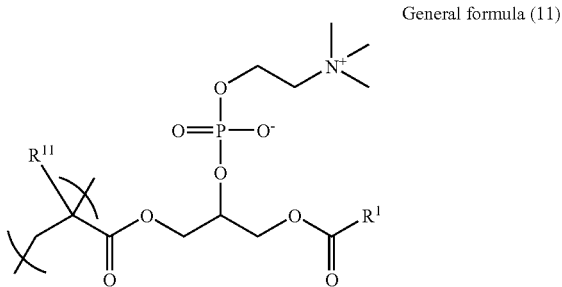

wherein R$^{11}$ represents hydrogen atom or methyl group, and R$^1$ represents hydrogen atom or a substituted or unsubstituted alkyl group.
[11] A polymer comprising the structural unit represented by general formula (12) below:

General formula (12)

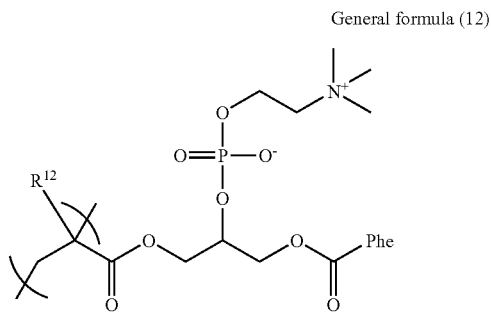

wherein R$^{12}$ represents hydrogen atom or methyl group; Phe represents an iodine-substituted phenyl group comprising two or more iodine atoms, with the iodine-substituted phenyl group being optionally substituted with a substituent selected from the group consisting of amino group, carboxyl group, a halogen atom, —NR$^3$(C=O)R$^4$, —(C=O)OR$^5$, —(C=O)NR$^6$R$^7$ (with each of R$^3$ to R$^7$ representing hydrogen atom, a substituted or unsubstituted alkyl group, or a substituted or unsubstituted aryl group), a substituted or unsubstituted alkyl group, and a substituted or unsubstituted aryl group.
[12] A polymer comprising the structural unit represented by general formula (11) and the unit structure represented by general formula (12) below:

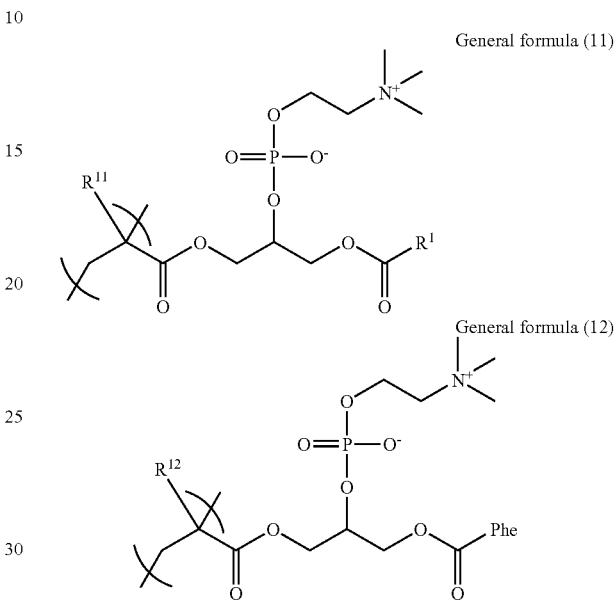

wherein each of R$^{11}$ and R$^{12}$ independently represents hydrogen atom or methyl group; R$^1$ represents hydrogen atom or a substituted or unsubstituted alkyl group; and Phe represents an iodine-substituted phenyl group comprising two or more iodine atoms, with the iodine substituted phenyl group being optionally substituted with a substituent selected from the group consisting of amino group, carboxyl group, a halogen atom, —NR$^3$(C=O)R$^4$, —(C=O)OR$^5$, —(C=O)NR$^6$R$^7$ (with each of R$^3$ to R$^7$ representing a hydrogen atom, a substituted or unsubstituted alkyl group, or a substituted or unsubstituted aryl group), a substituted or unsubstituted alkyl group, and a substituted or unsubstituted aryl group.

BEST MODE OF CARRYING OUT THE INVENTION

The present invention will be described in detail below.
Ranges that are given in the present specification and consist of two numbers separated by the word "to" are intended to include the numbers as lower and upper limits, respectively.
When the descriptive phrasing "substituted or unsubstituted" or "optionally substituted" is employed for a given group in the present specification, the phrasing means that the group may be substituted with one or more groups. However, the number, substitution position, and type of bonded substituent are not specifically limited unless specifically stated. When two or more substituents are present in a given group, the substituents may be identical or different. When a given group has a substituent in the present specification, examples of the substituent include a halogen atom (in the present specification, a "halogen atom" means a fluorine atom, chlorine atom, bromine atom, or iodine atom); an alkyl group (in the present specification, an "alkyl group" means an alkyl group that is linear, branched, or some combination thereof; a cycloalkyl group; an alkenyl group (in the present specification, an "alkenyl group" means an alkenyl group that is linear, branched, or some combination thereof; a cycloalkenyl group; an alkynyl group; an aryl group; a heterocyclic group; cyano group; hydroxyl groups; nitro group; a carboxyl group; a carbamoyl group; an alkoxy group; an aryloxy group; a heterocyclic oxy group; an acyloxy group; a carbamoyloxy group; a carbonyloxy group; an amino group (including an anilino group); a carbonylamino group; an acyl group; an aryloxycarbonyl group; an alkoxycarbonyl group; a carbamoyl group; an aryl or heterocyclic azo group; an imido group; a substituent in the form of any one of the above substituents that is substituted with any one or more of the above substituents; and a substituent in the form of any one of the above substituents, that has been substituted with any one of the above substituents, that has itself been further substituted with any one or more of the above substituents.

In general formula (I), $R^{10}$ represents hydrogen atom or methyl group. Although not a specific limitation, $R^{10}$ is preferably methyl group. The same holds true for $R^{11}$ in general formula (11) and $R^{12}$ in general formula (12).

In general formula (I), X represents —O—, —S—, —NR$^2$—, or —O(C=O)— (with $R^2$ representing hydrogen atom, a substituted or unsubstituted alkyl group, or a substituted or unsubstituted aryl group). X preferably represents —O—, —NH—, or —O(C=O)—, and more preferably represents —O(C=O)—.

The total number of carbon atoms in an unsubstituted alkyl group represented by R or $R^1$ is preferably 1 to 30, more preferably 1 to 20. Examples of alkyl groups represented by R or $R^1$ include methyl group, ethyl group, propyl group, i-propyl group, butyl group, s-butyl group, t-butyl group, hexyl group, octyl group, 2-ethylhexyl group, decyl group, undecyl group, dodecyl group, tridecyl group, tetradecyl group, pentadecyl group, hexadecyl group, and heptadecyl group.

R or $R^1$ may represent a substituted alkyl group in the form of the above alkyl group having one or more substituents. Examples of such substituted alkyl groups include chlorobutyl group, benzyl group, 2-ethynylpropyl group, phenylethyl group, cyanopropyl group, methoxyethyl group, hydroxymethyl group, aminomethyl group, chlorodecyl group, ethynylhexadecyl group, phenylundecyl group, cyanooctyl group, methoxypentadecyl group, hydroxytetradecyl group, aminotridecyl group, 1-methoxycarbamoylethyl group, 1-(-N-(2-phenyl-1-carboxy)ethylcarbamoyl)ethyl group, and 2-ethoxycarbonylbutyl groups. Examples of the substituted alkyl groups further include the compounds incorporating phenyl groups in the examples of the above substituted alkyl group, wherein the phenyl groups are each substituted with 2 or more, preferably 3 or more, iodine atoms. The total number of carbon atoms of the substituted alkyl group is preferably 2 to 40, more preferably 2 to 25.

Neither the position nor number of double bonds in an unsubstituted alkenyl group represented by R is specifically limited. The double bond may be of E or Z configuration. When multiple double bonds are present, there may be a mixture of E and Z configurations. The total number of carbon atoms of an alkenyl group represented by R is preferably 2 to 30, more preferably 5 to 20. Examples of unsubstituted alkenyl groups include vinyl group, 1-propenyl group, 2-propenyl group, 3-butenyl group, pentenyl group, 2-hexenyl group, hexadienyl group, 5-dodecenyl group, 10-pentadecenyl group, 14-hexadecenyl group, and 9-heptadecenyl group. R may represent a substituted alkenyl group in the form of the above unsubstituted alkenyl group having one or more substituents.

The total number of carbon atoms of an unsubstituted cycloalkyl group represented by R is preferably 3 to 20, more preferably 5 to 10. Examples of unsubstituted cycloalkyl groups include cyclopropyl group, cyclobutyl group, cyclopentyl group, cyclohexyl group, and cycloheptyl groups. R may represent a substituted cycloalkyl group in the form of the above unsubstituted cycloalkyl group having one or more substituents. The total number of carbon atoms of a cycloalkenyl group represented by R is preferably 4 to 20, more preferably 5 to 10. An example of an unsubstituted cycloalkenyl group includes a cyclohexenyl group R may represent a substituted cycloalkenyl group in the form of the above unsubstituted cycloalkenyl group having one or more substituents.

An unsubstituted heterocyclic group represented by R may be a saturated or unsaturated aliphatic heterocyclic group or aromatic heterocyclic group. The hetero atoms in the heterocyclic group are not specifically limited, with one or more atoms selected from among oxygen atom, sulfur atom, and nitrogen atom being desirable. Examples of heterocyclic groups include cyclic groups derived from furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, indole, indoline, isoindole, isoindoline, indazole, benzoimidazole, benzotriazole, tetrahydroisoquinoline, benzothiazolinone, benzoxazolinone, purine, quinolidine, quinoline, phthalazine, naphthyridine, quinoxaline, quinozoline, cinnoline, pteridine, oxazole, oxazolidine, isoxazole, isoxazolidine, oxadiazol, thiazol, benzothiazol, thiadiridine, isothiazol, isothiazolidine, benzodioxol, dioxane, benzodioxane, dithiane, morpholine, thiomorpholine, phthalimide, homopiperidinyl, homopiperazinyl, and the like. The bonding position on the ring is not limited. R may represent a substituted heterocyclic group in the form of the above unsubstituted heterocyclic group having one or more substituents.

The total carbon number of an unsubstituted aryl group represented by R or any of $R^1$ to $R^7$ is preferably 6 to 30, more preferably 6 to 20. Examples of such aryl groups include phenyl group, naphthyl group, and anthracenyl group. R or any of $R^1$ to $R^7$ may represent a substituted aryl group in the form of the above unsubstituted aryl group having one or more substituents. Examples of substituted aryl groups include methoxyphenyl group, chlorophenyl group, hydroxyphenyl group, aminophenyl group, ethylphenyl group, biphenyl group, nonylphenyl group, octylphenyl group, fluorophenyl group, and iodophenyl group.

A substituted aryl group represented by R is preferably an iodine-substituted phenyl group including two or more iodine atoms. The number of iodine atoms in the iodine-substituted phenyl group is preferably three. Such an iodine-substituted phenyl group may have in addition to iodine other one or more substituents selected from among amino group, carboxyl group, a halogen atom, —NR$^3$(C=O)R$^4$, —(C=O)OR$^5$, —(C=O)NR$^6$R$^7$ (wherein each of $R^3$ to $R^7$ represents hydrogen atom, a substituted or unsubstituted alkyl group, or a substituted or unsubstituted aryl group), a substituted or unsubstituted alkyl group, and a substituted or unsubstituted aryl group.

The number of carbon atoms of an unsubstituted alkyl group represented by any of $R^2$ to $R^7$ or the unsubstituted alkyl group substituent on a substituted aryl group represented by R is preferably 1 to 20, more preferably 1 to 6. The substituent in a substituted aryl group represented by R, or any of $R^3$ to $R^7$, may be a substituted alkyl group.

When the compound represented by general formula (I) is an aryl group, preferably comprising a phenyl group, the aryl group preferably have a substituent in the form of iodine. Preferably two or more iodine atoms, more preferably three iodine atoms, are substituted. Such a compound represented by general formula (I), or a polymer obtained by polymerizing such a compound, can be administered into the body and employed as an X-ray imaging agent.

The following compounds are specific examples of the compound represented by general formula (I):

Compound 1
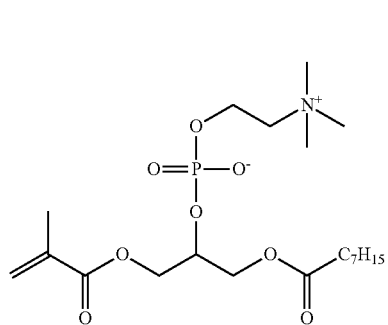

Compound 2
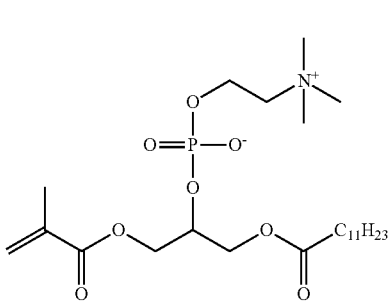

Compound 3
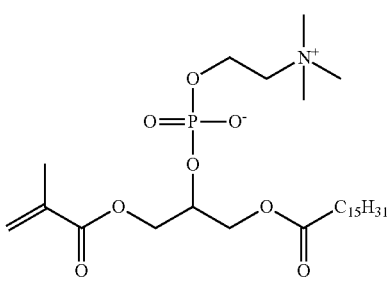

Compound 4
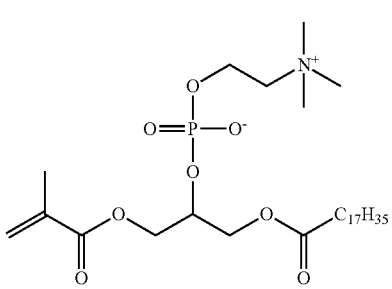

Compound 5
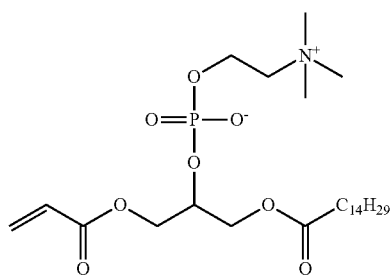

Compound 6
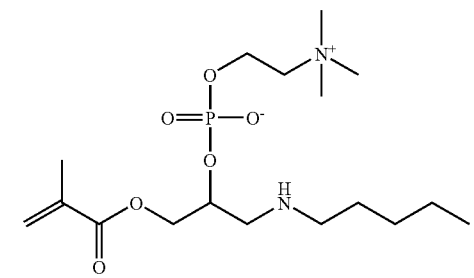

Compound 7
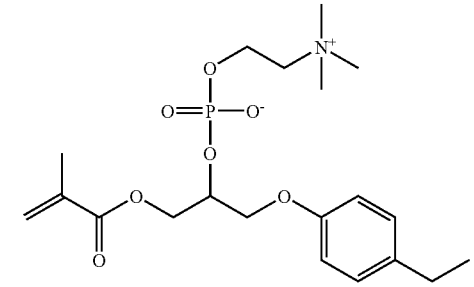

Compound 8
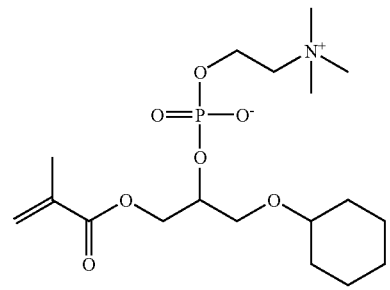

Compound 9

Compound 10
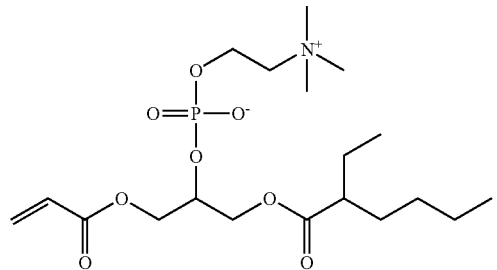
Compound 11
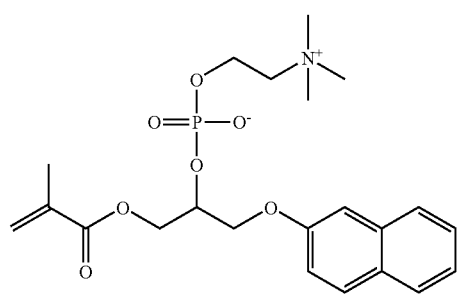
Compound 12
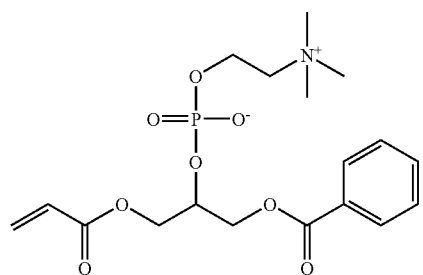
Compound 13
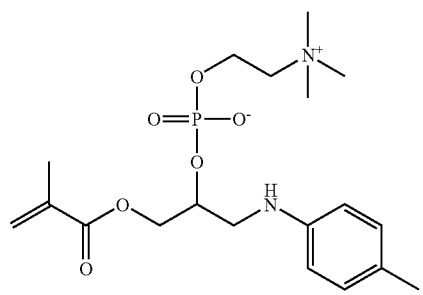
Compound 14
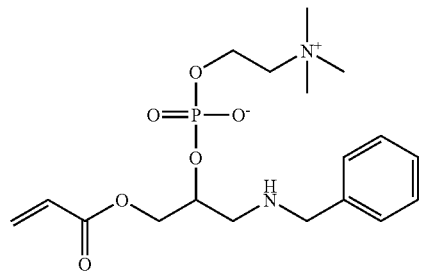
Compound 15
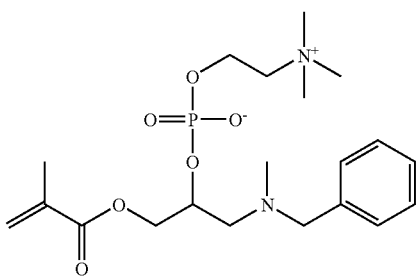
Compound 16
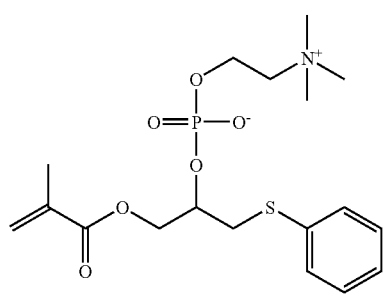
Compound 17
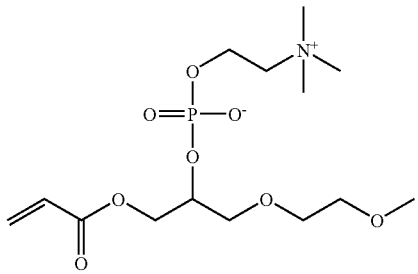
Compound 18
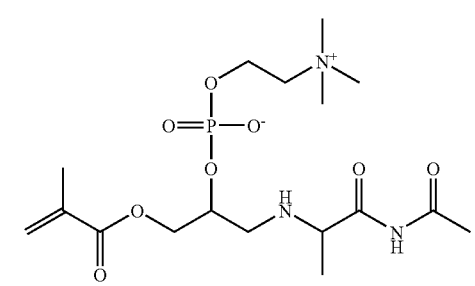
Compound 19
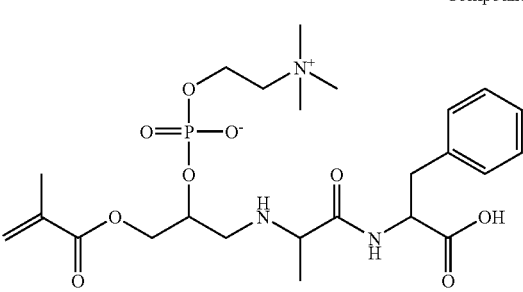

Compound 20
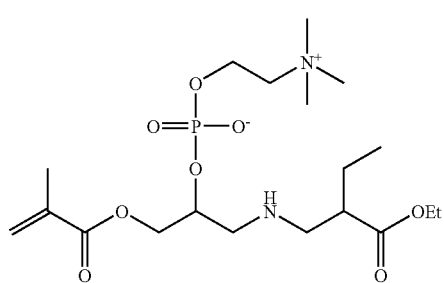
Compound 21
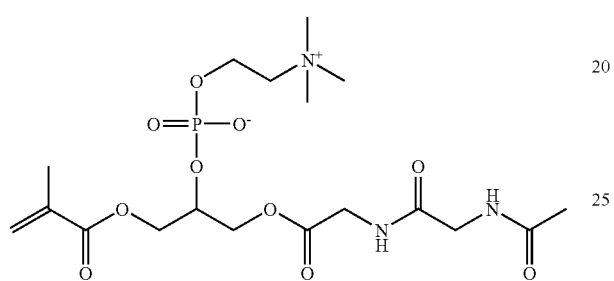
Compound 22
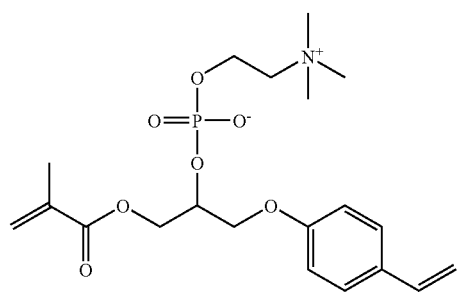
Compound 23
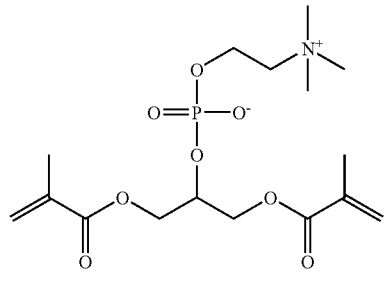
Compound 24
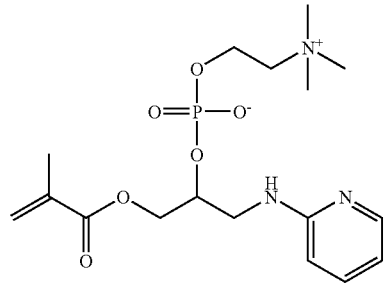
Compound 25
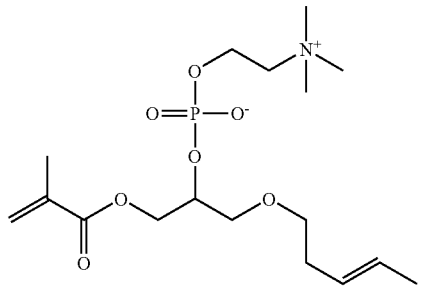
Compound 26
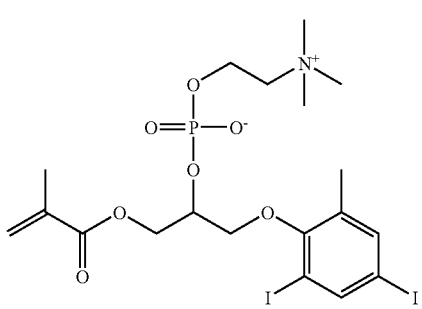
Compound 27
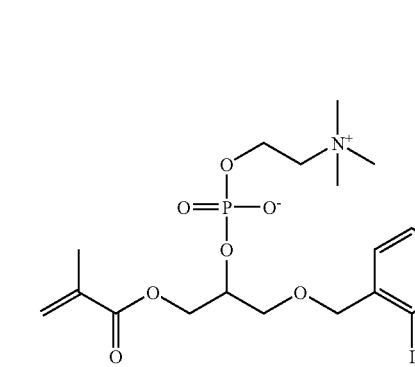
Compound 28
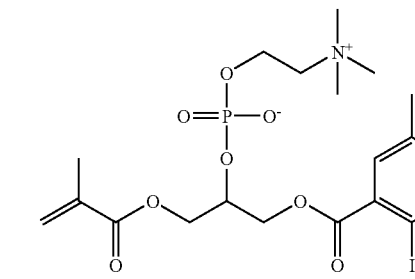
Compound 29
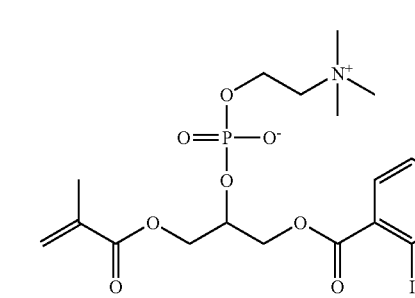

Compound 30

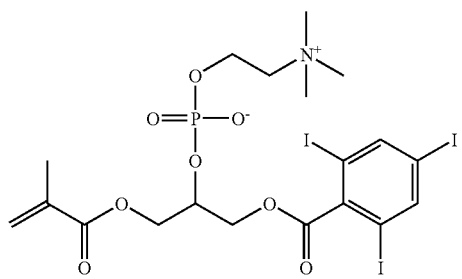

Compound 31

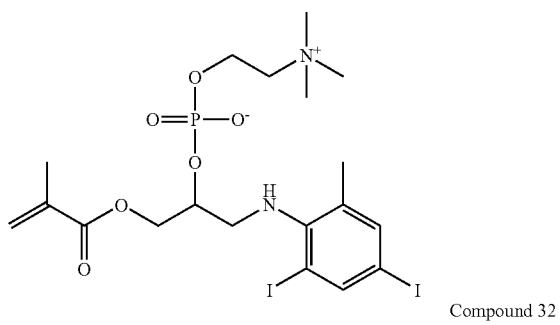

Compound 32

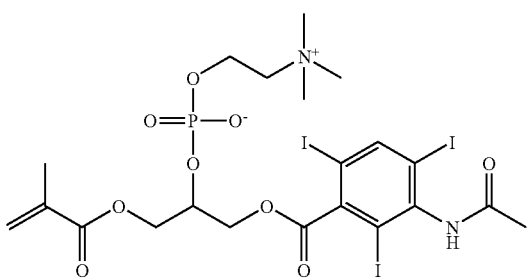

The compound represented by general formula (I) can generally be manufactured as set forth below.

Glycidyl(meth)acrylate and a carboxylic acid are added to a reaction solvent (an alcohol, acetone, methyl ethyl ketone, cyclohexanone, dimethyl acetamide, dimethyl formamide, dimethyl sulfoxide, sulfolane, N-methylpyrrolidone, or the like). As needed, a catalyst (an ammonium salt such as tetrabutylammonium bromide) is added, and the mixture is reacted with heating to 50° C. or higher but not greater than 120° C. to produce an intermediate.

Following the reaction, processing can be suitably conducted by methods known to persons having ordinary skill in the art, such as the methods given in the examples.

The intermediate can be reacted with 2-chloro-2-oxo-1,3, 2-dioxaphospholane to obtain the compound represented by general formula (I). This reaction can be suitably conducted, for example, by the method set forth in the examples. A temperature of −70° C. or higher, but not higher than 0° C., suffices during the reaction. A reaction solvent in the form of methylene chloride, chloroform, acetone, tetrahydrofuran, diethyl ether, 1,2-dichloroethane, chlorobenzene, or the like can be suitably selected.

The compound represented by general formula (I) can be polymerized, for example, by charging a solvent and the compound represented by general formula (I) to a reaction vessel and suitably heating them in the presence of a polymerization initiator. In copolymerization, it suffices for both of the monomer compounds being copolymerized to be present in the above solution.

The only requirement of the solvent employed in polymerization is that it be capable of dissolving the compound represented by general formula (I), and as needed, the monomers being copolymerized and a polymerization initiator. Examples of solvents include water, methanol, ethanol, propanol, butanol, tetrahydrofuran, acetonitrile, acetone, benzene, toluene, dimethylformamide, and mixtures thereof.

The polymerization initiator employed in polymerization is not specifically limited. However, a radical polymerization initiator is preferable. Examples of radical polymerization initiators include aliphatic azo compounds such as 2'-azobisisobutyronitrile and azobismalenonitrile, and organic peroxides such as benzoyl peroxide, lauroyl peroxide, ammonium peroxide, and potassium peroxide.

In polymerization, two or more compounds represented by general formula (I) can be copolymerized, or a compound represented by general formula (I) and a compound not represented by general formula (I) can be copolymerized. The compound that can be used for copolymerization with a compound represented by general formula (I) is not specifically limited and can be suitably selected based on the objective. Examples include (meth)acrylic acid esters, (meth)acrylamides, vinyl ethers, and styrenes (for example, styrene and styrene derivatives).

Examples of the above (meth)acrylic acid esters include methyl(meth)acrylate, ethyl(meth)acrylate, n-propyl(meth)acrylate, isopropyl(meth)acrylate, n-butyl(meth)acrylate, isobutyl(meth)acrylate, t-butyl(meth)acrylate, n-hexyl (meth)acrylate, cyclohexyl(meth)acrylate, t-butylcyclohexyl (meth)acrylate, 2-ethylhexyl(meth)acrylate, t-octyl(meth) acrylate, dodecyl(meth)acrylate, hexadecyl(meth)acrylate, pentadecyl(meth)acrylate, octadecyl(meth)acrylate, acetoxyethyl(meth)acrylate, phenyl(meth)acrylate, 2-methoxyethyl(meth)acrylate, 2-ethoxyethyl(meth)acrylate, 2-(2-metoxyethoxy)ethyl(meth)acrylate, benzyl(meth)acrylate, diethyleneglycol monomethylether(meth)acrylate, diethyleneglycol monoethylether(meth)acrylate, diethyleneglycol monophenylether(meth)acrylate, trimethyleneglycol monomethylether(meth)acrylate, triethyleneglycol monoethylether(meth)acrylate, polyethyleneglycol monomethylether(meth)acrylate, polyethyleneglycol monoethylether (meth)acrylate, beta-phenoxyethoxyethyl acrylate, nonylphenoxypolyethyleneglycol(meth)acrylate, dicyclopentanyl(meth)acrylate, dicyclopentenyl(meth)acrylate, dicyclopentyloxyethyl(meth)acrylate, trifluoroethyl(meth) acrylate, octafluoropentyl(meth)acrylate, perfluorooctylethyl(meth)acrylate, tribromophenyl(meth)acrylate, and tribromophenyloxyethyl(meth)acrylate.

Examples of the above (meth)acrylamides include (meth) acrylamide, N-methyl meth(acrylamide), N-ethyl(meth) acrylamide, N-propyl(meth)acrylamide, N-isopropyl(meth) acrylamide, N-n-butyl(meth)acrylamide, N-t-butyl(meth) acrylamide, N-cyclohexyl(meth)acrylamide, N-(2-methoxyethyl)(meth)acrylamide, N,N-dimethyl(meth) acrylamide, N,N-diethyl(meth)acrylamide, N-phenyl(meth) acrylamide, N-benzyl(meth)acrylamide, (meth) acryloylmorpholine, and diacetone acrylamide.

Examples of the above styrenes include styrene and styrene derivatives (such as methylstyrene, dimethylstyrene, trimethylstyrene, ethylstyrene, isopropylstyrene, butylstyrene, methoxystyrene, butoxystyrene, acetoxystyrene, chlorostyrene, dichlorostyrene, bromostyrene, hydroxystyrene protected by groups (such as t-Boc) that can be removed by an acidic substance, vinyl methylbenzoate, and alpha-methylstyrene).

Examples of the above vinyl ethers include methyl vinyl ether, butyl vinyl ether, hexyl vinyl ether, and methoxyethyl vinyl ether.

The molar ratio of the compound represented by general formula (I) to the compound not represented by general formula (I) during copolymerization is preferably 100:0 to 20:80, more preferably 100:0 to 30:70, and further preferably, 100:0 to 50:50.

The molecular weight of the polymer obtained by polymerizing the compound represented by general formula (I) is not specifically limited, but is preferably 1,000 to 100,000.

Examples of polymers obtained by polymerizing the compound represented by general formula (I) include polymers containing the structural unit represented by general formula (11) below:

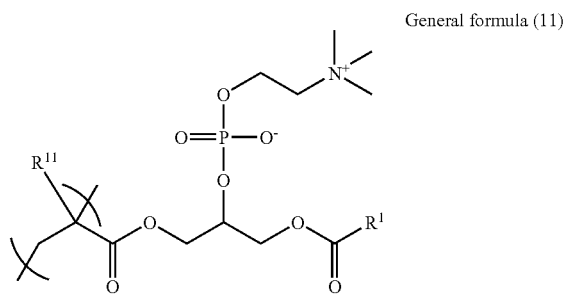

General formula (11)

(wherein $R^{11}$ represents hydrogen atom or methyl group and $R^1$ represents a hydrogen atom or a substituted or unsubstituted alkyl group) and polymers containing the structural unit represented by general formula (12) below:

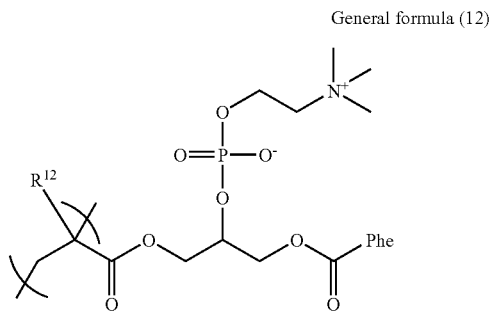

General formula (12)

(wherein $R^{12}$ represents hydrogen atom or methyl group and Phe represents an iodine-substituted phenyl group having two or more iodine atoms, with the iodine-substituted phenyl group being optionally substituted with a substituent selected from the group consisting of amino group, carboxyl group, a halogen atom, —$NR^3(C=O)R^4$, —$(C=O)OR^5$, —$(C=O)NR^6R^7$ (with each of $R^3$ to $R^7$ representing an alkyl group or an aryl group), an alkyl group, and an aryl group).

A polymer containing both the structural unit represented by general formula (11) and the structural unit represented by general formula (12) is also preferable. The molar ratio of these structural units (general formula (11): general formula (12)) is preferably 0:100 to 50:50, more preferably 0:100 to 40:60, and further preferably, 0:100 to 30:70.

Particles can be formed in an aqueous solution of the polymer obtained by polymerizing the compound represented by general formula (I) prepared as set forth above. The diameter of the particles is preferably 4 to 400 nm, more preferably 4 to 200 nm.

Such polymer particles can be employed as imaging agents, for example. By way of example, an X-ray imaging agent can be prepared with polymer particles produced using the compound represented by general formula (I) containing iodine.

An imaging agent of high biocompatibility can be prepared by forming polymer particles with compounds having an imaging effect, for example. A paramagnetic metal compound is an example of a compound having an imaging effect. Within the particle, the compound having an imaging effect can be enveloped in the above polymer, or the component having an imaging effect can form the membrane of the particle with the polymer.

A tumor-selective imaging agent can be provided by linking an antibody, such as an antibody to a protein that is overexpressed at tumor sites, to the surface of the polymer particle. The polymer particle of the present invention is of small diameter and can be used to prepare an imaging agent that is resistant to capture by the reticuloendothelial system.

EXAMPLES

The present invention is described in greater detail below through examples. However, the scope of the present invention is not limited to the examples given below.

Example 1

To a reaction vessel were charged glycidyl methacrylate (made by Tokyo Chemical Industry Co., Ltd.) (3 weight parts), dodecanoic acid (made by Tokyo Chemical Industry Co., Ltd.) (4.3 weight parts), tetrabutylammonium bromide (made by Wako Pure Chemical Industries, Ltd.) (0.7 weight part), and dimethylacetamide (made by Wako Pure Chemical Industries, Ltd.) (50 weight parts). The mixture obtained was heated to 90° C. in an oil bath and stirred for 2 hours. Subsequently, 300 weight parts of water and 80 weight parts of ethyl acetate (made by Wako Pure Chemical Industries, Ltd.) were added, and the solution was separated. The organic solvent layer was washed with 200 weight parts of saturated brine and then dried with magnesium sulfate. The magnesium sulfate was removed by filtration, and the organic solvent was distilled off under vacuum. The crude product obtained was purified by silica gel chromatography, yielding 5.4 weight parts (a yield of 75 percent) of an oily intermediate 1A.

Next, oily intermediate 1A (4 weight parts), triethylamine (made by Wako Pure Chemical Industries, Ltd.) (1.5 weight parts), and methylene chloride (made by Wako Pure Chemical Industries, Ltd.) (30 weight parts) were added to a separate reaction vessel that had been cooled to −20° C. in a nitrogen atmosphere. To the mixture obtained were added through a dropping funnel 2.1 weight parts of 2-chloro-2-oxo-1,3,2-dioxaphospholane (CAS 6609-64-9) (made by Wako Pure Chemical Industries, Ltd.). The mixture was stirred for 2 hours and then filtered to remove the white crystals that had been produced. The solvent was removed by vacuum distillation. The residue was charged to a reaction vessel. Acetonitrile (made by Wako Pure Chemical Industries, Ltd.) (30 weight parts) and trimethylamine (made by Aldrich Chemical Co.) (3 weight parts) were added and the mixture was stirred for 24 hours at 60° C. After completion of the reaction, the reaction solution was filtered to remove the solid material, and the solvent was distilled off under vacuum. The crude product obtained was purified by reverse phase silica gel chromatography, yielding 1.8 weight parts of Specific Compound Example 2 (a yield of 30 percent).

$^1$H-NMR (300 MHz)CDCl$_3$ 6.11 (s, 1H), 5.58 (s, 1H), 4.65-4.50 (m, 1H), 4.40-4.24 (m, 6H), 3.75 (s, 2H), 3.35 (s, 9H), 2.30 (t, 2H), 1.91 (s, 3H), 1.60 (t, 2H), 1.35-1.20 (m, 16H), 0.89 (t, 3H)

Example 2

To a reaction vessel were charged glycidyl methacrylate (made by Tokyo Chemical Industry Co., Ltd.) (3 weight parts), palmitic acid (made by Tokyo Chemical Industry Co., Ltd.) (5.4 weight parts), tetrabutylammonium bromide (made by Wake Pure Chemical Industries, Ltd.) (0.7 weight part), and dimethylacetamide (made by Wake Pure Chemical Industries, Ltd.) (50 weight parts). The mixture obtained was heated to 90° C. in an oil bath and stirred for 2 hours. Subsequently, water (300 weight parts) and ethyl acetate (made by Wake Pure Chemical Industries, Ltd.) (80 weight parts) were added and the solution was separated. The organic solvent layer was washed with saturated brine (200 weight parts) and dried with magnesium sulfate. The magnesium sulfate was removed by filtration and the organic solvent was distilled off under vacuum. The crude product obtained was purified by silica gel chromatography, yielding 4.6 weight parts (a yield of 55 percent) of an oily intermediate 2A.

Next, oily intermediate 2A (4 weight parts), triethylamine (made by Wake Pure Chemical Industries, Ltd.) (1.1 weight parts), and methylene chloride (made by Wake Pure Chemical Industries, Ltd.) (15 weight parts) were added to a separate reaction vessel that had been cooled to −20° C. in a nitrogen atmosphere. To the mixture obtained was added 2-chloro-2-oxo-1,3,2-dioxaphospholane (CAS 6609-64-9) (made by Wako Pure Chemical Industries, Ltd.) (1.5 weight parts) through a dropping funnel. The mixture was stirred for 2 hours and then filtered to remove the white crystals that had been produced. The solvent was removed by vacuum distillation. The residue was charged to a reaction vessel. Acetonitrile (made by Wake Pure Chemical Industries, Ltd.) (30 weight parts) and trimethylamine (made by Aldrich Chemical Co.) (3 weight parts) were added and the mixture was stirred for 24 hours at 60° C. After completion of the reaction, the reaction solution was filtered to remove the solid material, and the solvent was distilled off under vacuum. The crude product obtained was purified by reverse phase silica gel chromatography, yielding 3.8 weight parts of Specific Compound Example 3 (a yield of 67 percent).

$^1$H-NMR (300 MHz) CDCl$_3$ 6.11 (s, 1H), 5.58 (s, 1H), 4.65-4.50 (m, 1H), 4.40-4.24 (m, 6H), 3.75 (s, 2H), 3.35 (s, 9H), 2.30 (t, 2H), 1.91 (s, 3H), 1.60 (t, 2H), 1.35-1.20 (m, 24H), 0.89 (t, 3H)

Example 3

To a reaction vessel were charged glycidyl methacrylate (made by Tokyo Chemical Industry Co., Ltd.) (3 weight parts), 2,3,5-triiodobenzoic acid (made by Tokyo Chemical Industry Co., Ltd.) (10.6 weight parts), tetrabutylammonium bromide (made by Wake Pure Chemical Industries, Ltd.) (0.7 weight part), and dimethylacetamide (made by Wake Pure Chemical Industries, Ltd.) (50 weight parts). The mixture obtained was heated to 90° C. in an oil bath and stirred for 2 hours. Subsequently, water (300 weight parts) and ethyl acetate (made by Wake Pure Chemical Industries, Ltd.) (80 weight parts) were added and the solution was separated. The organic solvent layer was washed with saturated brine (200 weight parts) and dried with magnesium sulfate. The magnesium sulfate was removed by filtration and the organic solvent was distilled off under vacuum. The crude product obtained was purified by silica gel chromatography, yielding 10.9 weight parts (a yield of 80 percent) of an oily intermediate 3A.

Next, oily intermediate 3A (8 weight parts), triethylamine (made by Wako Pure Chemical Industries, Ltd.) (1.3 weight parts), and methylene chloride (made by Wako Pure Chemical Industries, Ltd.) (30 weight parts) were added to a separate reaction vessel that had been cooled to −20° C. in a nitrogen atmosphere. To the mixture obtained was added 2-chloro-2-oxo-1,3,2-dioxaphospholane (CAS 6609-64-9) (made by Wako Pure Chemical Industries, Ltd.) (1.8 weight parts) through a dropping funnel. The mixture was stirred for 2 hours and then filtered to remove the white crystals that had been produced. The solvent was removed by vacuum distillation. The residue was charged to a reaction vessel. Acetonitrile (made by Wako Pure Chemical Industries, Ltd.) (30 weight parts) and trimethylamine (made by Aldrich Chemical Co.) (3 weight parts) were added to the reaction vessel and the mixture was stirred for 24 hours at 60° C. After completion of the reaction, the reaction solution was filtered to remove the solid material, and the solvent was distilled off under vacuum. The crude product obtained was purified by reverse phase silica gel chromatography, yielding 6.5 weight parts of Specific Compound Example 28 (a yield of 65 percent).

$^1$H-NMR (300 MHz) CDCl$_3$ 8.25 (s, 1H), 7.76 (s, 1H), 6.11 (s, 1H), 5.58 (s, 1H), 4.75-4.28 (m, 7H), 3.75 (s, 2H), 3.30 (s, 9H), 1.91 (s, 3H)

Example 4

To a reaction vessel were charged glycidyl methacrylate (made by Tokyo Chemical Industry Co., Ltd.) (3 weight parts), acetrizoic acid (CAS-85-36-9) (made by Tokyo Chemical Industry Co., Ltd.) (11.8 weight parts), tetrabutylammonium bromide (made by Wako Pure Chemical Industries, Ltd.) (0.7 weight part), and dimethylacetamide (made by Wako Pure Chemical Industries, Ltd.) (50 weight parts). The mixture obtained was heated to 90° C. in an oil bath and stirred for 2 hours. Subsequently, water (300 weight parts) and ethyl acetate (made by Wake Pure Chemical Industries, Ltd.) (80 weight parts) were added and the solution was separated. The organic solvent layer was washed with saturated brine (200 weight parts) and dried with magnesium sulfate. The magnesium sulfate was removed by filtration and the organic solvent was distilled off under vacuum. The crude product obtained was purified by silica gel chromatography, yielding 9.4 weight parts (a yield of 64 percent) of an oily intermediate 4A.

Next, oily intermediate 4A (6 weight parts), triethylamine (made by Wako Pure Chemical Industries, Ltd.) (0.9 weight part), and methylene chloride (made by Wake Pure Chemical Industries, Ltd.) (30 weight parts) were added to a separate reaction vessel that had been cooled to −20° C. in a nitrogen atmosphere. To the mixture obtained was added 2-chloro-2-oxo-1,3,2-dioxaphospholane (CAS 6609-64-9) (made by Wake Pure Chemical Industries, Ltd.) (1.4 weight parts) through a dropping funnel. The mixture was stirred for 2 hours and then filtered to remove the white crystals that had been produced. The solvent was removed by vacuum distillation. The product obtained was charged to a reaction vessel. Acetonitrile (made by Wako Pure Chemical Industries, Ltd.) (30 weight parts) and trimethylamine (made by Aldrich Chemical Co.) (3 weight parts) were added to the reaction vessel and the mixture was stirred for 24 hours at 60° C. After completion of the reaction, the reaction solution was filtered to remove the solid material, and the solvent was distilled off under vacuum. The crude product obtained was purified by reverse phase silica gel chromatography, yielding 3.8 weight parts of Specific Compound Example 32 (a yield of 50 percent).

$^1$H-NMR (300 MHz) CDCl$_3$ 8.25 (s, 1H), 7.90 (br, 1H), 6.11 (s, 1H), 5.58 (s, 1H), 4.75-4.28 (m, 7H), 3.75 (s, 2H), 2.17 (s, 3H), 1.91 (s, 3H)

Example 5

To a reaction vessel were charged Specific Compound Example 3 (3 weight parts), stearyl methacrylate (made by Tokyo Chemical Industry Co., Ltd.) (1.8 weight parts), n-propanol (made by Wako Pure Chemical Industries, Ltd.) (2 weight parts), and V-601 (made by Wako Pure Chemical Industries, Ltd.) (0.002 weight part). Under a nitrogen atmosphere, stirring was conducted for 8 hours at an internal temperature of 80° C. After completion of the reaction, the reaction solution was slowly introduced into acetone (100 weight parts), yielding 2.6 weight parts of a white solid.

A 0.1 weight part of the white solid was dissolved in 0.4 weight part of n-propanol (made by Wako Pure Chemical Industries, Ltd.) and heated to 60° C. A 1.6 weight part quantity of pure water was added to the solution. Subsequently, the mixture was stirred for 20 minutes, yielding a polymer particle dispersion. The mean particle size of the polymer particles present in the dispersion was 153 nm as measured with a particle diameter measuring device (UPA-EX150 made by Nikkiso Co., Ltd.).

Example 6

To a reaction vessel were charged Specific Compound Example 28 (0.025 weight part), n-propanol (Wako Pure Chemical Industries, Ltd.) (0.5 weight part), pure water (9.5 weight parts), and V-601 (made by Wako Pure Chemical Industries, Ltd.) (0.002 weight part). Under a nitrogen atmosphere, stirring was conducted for 8 hours at an internal temperature of 80° C. The reaction solution obtained was filtered through a gel (PD-10 columns: made by GE Healthcare), yielding a polymer particle dispersion. The mean particle size of the polymer particles present in the dispersion was 101 nm as measured with a particle diameter measuring device (UPA-EX150 made by Nikkiso Co., Ltd.).

EFFECT OF THE INVENTION

The present invention provides a new polymeric compound that is useful for manufacturing hydrophilic polymer materials of high biocompatibility.

What is claimed is:

1. A compound represented by general formula (I) below:

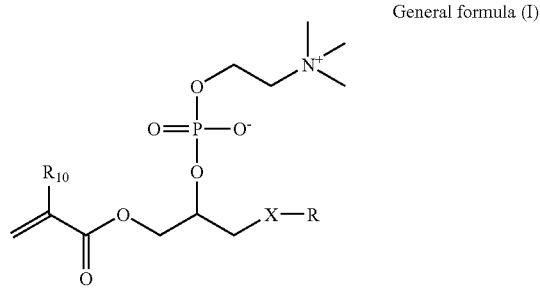

General formula (I)

wherein, $R^{10}$ represents hydrogen atom or methyl group;

X represents —O(C=O)—; and

R represents a substituted or unsubstituted aryl group.

2. The compound according to claim 1, wherein R comprises two or more iodine atoms.

3. The compound according to claim 1, wherein R is an iodine-substituted phenyl group comprising two or more iodine atoms, with the iodine-substituted phenyl group being optionally substituted with a substituent selected from the group consisting of amino group, carboxyl group, a halogen atom, —NR$^3$(C=O)R$^4$, —(C=O)OR$^5$, —(C=O)NR$^6$R$^7$ (with each of R$^3$ to R$^7$ representing hydrogen atom, a substituted or unsubstituted alkyl group, or a substituted or unsubstituted aryl group), a substituted or unsubstituted alkyl group, and a substituted or unsubstituted aryl group.

4. The compound according to claim 3, wherein R is an iodine-substituted phenyl group substituted with three iodine atoms.

* * * * *